United States Patent
Liu et al.

(10) Patent No.: US 9,212,140 B2
(45) Date of Patent: *Dec. 15, 2015

(54) (5S,8S)-3-(4'-CHLOR-3'-FLUOR-4-METHLYBIPHENYL-3-YL)-4-HYDROXY-8-METHOXY-1-AZASPIRO[4.5]DEC-3-EN-2-ONE (COMPOUND A) FOR TREATMENT

(75) Inventors: Ningshu Liu, Berlin (DE); Kai Thede, Berlin (DE); Philip Lienau, Berlin (DE); Arne Scholz, Berlin (DE); Christoph-Stephan Hilger, Berlin (DE); Ulf Bömer, Glienicke (DE); Maher Najjar, Langenzenn (DE); Knut Eis, Berlin (DE); Reiner Fischer, Monheim (DE); Wahed Ahmed Moradi, Monheim (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/983,165

(22) PCT Filed: Feb. 3, 2012

(86) PCT No.: PCT/EP2012/051895
§ 371 (c)(1),
(2), (4) Date: Oct. 16, 2013

(87) PCT Pub. No.: WO2012/104428
PCT Pub. Date: Aug. 9, 2012

(65) Prior Publication Data
US 2014/0031407 A1   Jan. 30, 2014

(30) Foreign Application Priority Data

Feb. 6, 2011 (KW) .................................... 14/2011
Feb. 8, 2011 (DE) ......................... 10 2011 011 040

(51) Int. Cl.
*A61K 31/4015* (2006.01)
*A61K 31/403* (2006.01)
*A61K 45/06* (2006.01)
*A01N 43/12* (2006.01)
*A01N 43/38* (2006.01)
*C07D 209/54* (2006.01)

(52) U.S. Cl.
CPC .................................. *C07D 209/54* (2013.01)

(58) Field of Classification Search
IPC ..................... A61K 31/403,45/06; A01N 43/48, A01N 43/12
See application file for complete search history.

(56) References Cited

U.S. PATENT DOCUMENTS 5,830,826 A * 11/1998 Fischer .................. A01N 43/36
504/195

FOREIGN PATENT DOCUMENTS

WO    WO 99/48869    * 9/1999

* cited by examiner

*Primary Examiner* — Shirley V Gembeh

(57) ABSTRACT

The invention relates to (5s,8s)-3-(4'-chloro-3'-fluoro-4-methylbiphenyl-3-yl)-4-hydroxy-8-methoxy-1-azaspiro[4.5]dec-3-en-2-one for therapeutic purposes, to pharmaceutical compositions and to their use in therapy, in particular for the prophylaxis and therapy of tumour disorders.

2 Claims, 4 Drawing Sheets

Fig: 1

Figure 1:
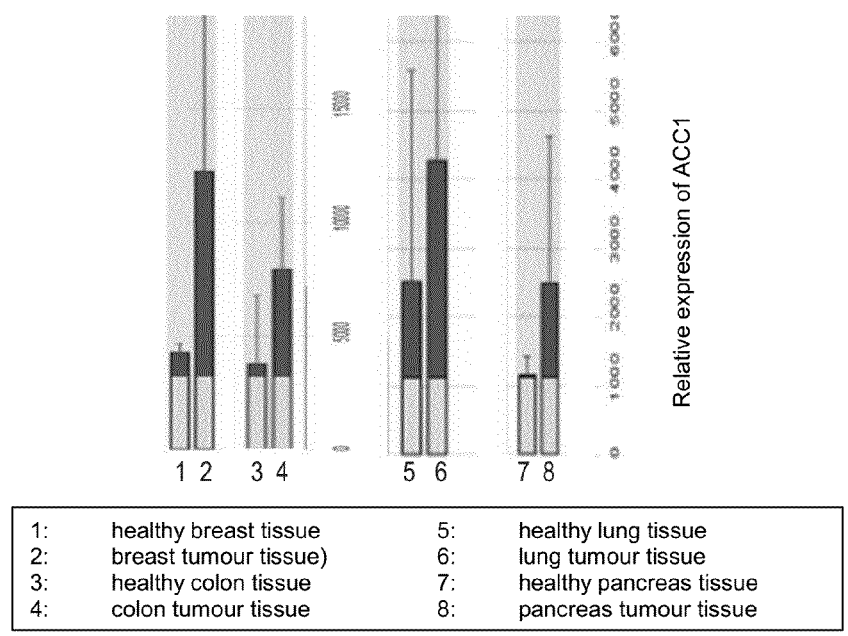

(5S,8S)-3-(4'-CHLOR-3'-FLUOR-4-METHLY-BIPHENYL-3-YL)-4-HYDROXY-8-METHOXY-1-AZASPIRO[4.5] DEC-3-EN-2-ONE (COMPOUND A) FOR TREATMENT

The present invention relates to (5s,8s)-3-(4'-chloro-3'-fluoro-4-methylbiphenyl-3-yl)-4-hydroxy-8-methoxy-1-azaspiro[4.5]dec-3-en-2-one (=compound A) for therapeutic purposes, to pharmaceutical compositions comprising compound A and to their use in therapy, in particular for the prophylaxis and/or therapy of tumour disorders.

Acetyl-CoA carboxylases (ACCs) play a key role in cellular fatty acid homeostasis. ACCs are biotin-containing enzymes which catalyze the carboxylation of acetyl-CoA to malonyl-CoA in an ATP-dependent manner (Kim, 1997; Harwood, 2005; Tong, 2005). This reaction, which proceeds as two semi-reactions, a biotin carboxylase (BC) reaction and a carboxyltransferase (CT) reaction, is the first initial step in the fatty acid biosynthesis and is the rate-determining step of the pathway. Two human ACC isoforms, ACC1 and ACC2, are known, which are encoded by different genes (LuTFI ABU-ELHEIGA et al, 1995, Jane WIDMER, et al. 1996). ACC1 is expressed in lipogenic tissue (liver, fatty tissue), is localized in the cytosol and fills the malonyl-CoA pool which serves as C2 unit donor for the de novo synthesis of long-chain fatty acids by FASN and subsequent chain elongation. ACC2 is expressed in particular in oxidative tissues (liver, heart, skeletal muscle) (Bianchi et al., 1990; Kim, 1997), is associated with the mitochondria, and regulates a second pool of malonyl-CoA. This regulates the fatty acid oxidation by inhibiting carnitinepalmitoyl transferase I, the enzyme which facilitates the import of long-chain fatty acids into the mitochondria for β-oxidation (Milgraum L Z, et al., 1997, Widmer J. et al., 1996). Both enzymes have very high sequence homology and are regulated in a similar manner by a combination of transcriptional, translational and prosttranslational mechanisms. In humans as well as in animals, the ACC activity is under the strict control of a number of dietary, hormonal and other physiological mechanisms such as, for example, through forward allosteric activation by citrate, feedback inhibition by long-chain fatty acids, reversible phosphorylation and/or inactivation or modulation of the enzyme production by modified gene expression.

ACC1 knockout mice are embryonally lethal (Swinnen, et al., 2006, Abu-Elheiga, et al. 2005). ACC2 knockout mice show reduced malonyl-CoA concentrations in skeletal and heart muscle, increased fatty acid oxidation in the muscle, reduced liver fat levels, reduced amounts of total body fat, increased levels of UCP3 in skeletal muscle (as a sign of increased energy output), reduced body weight, lower plasma concentrations of free fatty acids, reduced plasma glucose levels, reduced amounts of tissue glycogen, and they are protected against diet-induced diabetes and obesity (Abu-Elheiga et al., 2001, 2003; Oh et al., 2005).

In addition to being involved in the fatty acid synthesis in lipogenic tissues and the fatty acid oxidation in oxidative tissues, an upregulation of ACC and an increased lipogenesis was observed in many tumour cells (Swinnen, et al., 2004, Heemers, et al., 2000, Swinnen, et al., 2002, Rossi, et al., 2003, Milgraum, et al., 1997, Yahagi, et al., 2005). With high probability, this phenotype contributes in the development and progression of tumours; however, the associated regulatory mechanisms still have to be elucidated.

EPO454782 and U.S. Pat. No. 5,759,837 protect the use of fatty acid synthesis inhibitors to inhibit tumour cell growth. Cyclic ketoenols are not disclosed.

A number of substances capable of inhibiting plant and/or insect-ACC have been found.

PCT patent application PCT/EPP99/01787, published as WO 99/48869, which corresponds to the European patent EP 1 066 258 B1, relates to novel arylphenyl-substituted cyclic ketoenols, to a plurality of processes for their preparation and to their use as pesticides and herbicides.

Pharmaceutical properties of 3-acylpyrrolidine-2,4-diones have been described in the prior art (S. Suzuki et al. Chem. Pharm. Bull. 15 1120 (1967)). Furthermore, N-phenylpyrrolidine-2,4-diones have been synthesized by R. Schmierer and H. Mildenberger (Liebigs Ann. Chem. 1985, 1095). A biological activity of these compounds has not been described.

EP-A-0 262 399 and GB-A-2 266 888 disclose compounds of a similar structure (3-arylpyrrolidine-2,4-diones); however, these compounds have not been known to have any herbicidal, insecticidal or acaricidal activity. Known to have herbicidal, insecticidal or acaricidal activity are unsubstituted bicyclic 3-arylpyrrolidine-2,4-dione derivatives (EP-A-355 599, EP-A-415 211 and JP-A-12-053 670), and also substituted monocyclic 3-arylpyrrolidine-2,4-dione derivatives (EP-A-377 893 and EP-A-442 077).

Also known are polycyclic 3-arylpyrrolidine-2,4-dione derivatives (EP-A-442 073) and also 1H-arylpyrrolidinedione derivatives (EP-A-456 063, EP-A-521 334, EP-A-596 298, EP-A-613 884, EP-A-613 885, WO 95/01 971, WO 95/26 954, WO 95/20 572, EP-A-0 668 267, WO 96/25 395, WO 96/35 664, WO 97/01 535, WO 97/02 243, WO 97/36 868, WO 97/43275, WO 98/05638, WO 98/06721, WO 98/25928, WO 99/24437, WO 99/43649, WO 99/48869, WO 99/55673, WO 01/17972, WO 01/23354, WO 01/74770, WO 03/013249, WO 03/062244, WO 2004/007448, WO 2004/024 688, WO 04/065366, WO 04/080962, WO 04/111042, WO 05/044791, WO 05/044796, WO 05/048710, WO 05/049569, WO 05/066125, WO 05/092897, WO 06/000355, WO 06/029799, WO 06/056281, WO 06/056282, WO 06/089633, WO 07/048,545, DEA 102 00505 9892, WO 07/073,856, WO 07/096,058, WO 07/121,868, WO 07/140, 881, WO 08/067873, WO 08/067910, WO 08/067911, WO 08/138551, WO 09/015801, WO 09/039975, WO 09/049851, WO 09/115262, WO10/052161, WO 10/063378, WO 10/063670, WO10/063380, WO10/066780 and WO10/102758.

Moreover, ketal-substituted 1-H-arylpyrrolidine-2,4-diones are known from WO 99/16748 and (spiro)-ketal-substituted N-alkoxyalkoxy-substituted arylpyrrolidinediones are known from JP-A-14 205 984 and Ito M. et al. Bioscience, Biotechnology and Biochemistry 67, 1230-1238, (2003). Moreover, WO 06/024411 discloses herbicidal compositions which comprise ketoenols.

It is known that certain substituted $\Delta^3$-dihydrofuran-2-one derivatives have herbicidal properties (cf. DE-A-4 014 420). The synthesis of the tetronic acid derivatives used as starting materials (such as, for example, 3-(2-methylphenyl)-4-hydroxy-5-(4-fluorophenyl)-$\Delta^3$-dihydrofuranone-(2)) is likewise described in DE-A-4 014 420. Compounds of a similar structure are known from the publication Campbell et al., J. Chem. Soc., Perkin Trans. 1, 1985, (8) 1567-76, without any insecticidal and/or acaricidal activity being stated. 3-Aryl-$\Delta^3$-dihydrofuranone derivatives having herbicidal, acaricidal and insecticidal properties are furthermore known from: EP-A-528 156, EP-A-647 637, WO 95/26 954, WO 96/20 196, WO 96/25 395, WO 96/35 664, WO 97/01 535, WO 97/02 243, WO 97/36 868, WO 98/05 638, WO 98/06 721, WO 99/16 748, WO 98/25 928, WO 99/43 649, WO 99/48 869, WO 99/55 673, WO 01/23354, WO 01/74 770, WO 01/17 972, WO 04/024 688, WO 04/080 962, WO 04/111 042, WO 05/092 897, WO 06/000 355, WO 06/029 799, WO 07/048, 545, WO 07/073,856, WO 07/096,058, WO 07/121,868, WO 07/140,881, WO 08/067911, WO 08/083950, WO 09/015801, WO09/039975 and PCT/EP2010/003020.

3-Aryl-Δ³-dihydrothiophenone derivatives are known from WO 95/26 345, 96/25 395, WO 97/01 535, WO 97/02 243, WO 97/36 868, WO 98/05638, WO 98/25928, WO 99/16748, WO 99/43649, WO 99/48869, WO 99/55673, WO 01/17972, WO 01/23354, WO 01/74770, WO 03/013249, WO 04/080 962, WO 04/111 042, WO 05/092897, WO 06/029799 and WO 07/096,058.

Certain phenylpyrone derivatives which are unsubstituted in the phenyl ring are already known (cf. A. M. Chirazi, T. Kappe and E. Ziegler, Arch. Pharm. 309, 558 (1976) and K.-H. Boltze and K. Heidenbluth, Chem. Ber. 91, 2849). Phenylpyrone derivatives which are substituted in the phenyl ring and have herbicidal, acaricidal and insecticidal properties are described in EP-A-588 137, WO 96/25 395, WO 96/35 664, WO 97/01 535, WO 97/02 243, WO 97/16 436, WO 97/19 941, WO 97/36 868, WO 98/05638, WO 99/43649, WO 99/48869, WO 99/55673, WO 01/17972, WO 01/74770, WO 03/013249, WO 04/080 962, WO 04/111 042, WO 05/092897, WO 06/029799 and WO 07/096,058.

Certain 5-phenyl-1,3-thiazine derivatives which are unsubstituted in the phenyl ring are already known (cf. E. Ziegler and E. Steiner, Monatsh. 95, 147 (1964), R. Ketcham, T. Kappe and E. Ziegler, J. Heterocycl. Chem. 10, 223 (1973)). 5-Phenyl-1,3-thiazine derivatives which are substituted in the phenyl ring and have herbicidal, acaricidal and insecticidal properties are described in WO 94/14 785, WO 96/25 395, WO 96/35 664, WO 97/01 535, WO 97/02 243, WO 97/02 243, WO 97/36 868, WO 99/43649, WO 99/48869, WO 99/55673, WO 01/17972, WO 01/74770, WO 03/013249, WO 04/080 962, WO 04/111 042, WO 05/092897, WO 06/029799 and WO 07/096,058.

It is known that certain substituted 2-arylcyclopentanediones have herbicidal, insecticidal and acaricidal properties (cf., for example, U.S. Pat. Nos. 4,283,348; 4,338,122; 4,436,666; 4,526,723; 4,551,547; 4,632,698; WO 96/01 798; WO 96/03 366, WO 97/14 667 and also WO 98/39281, WO 99/43649, WO99/48869, WO 99/55673, WO 01/17972, WO 01/74770, WO 03/062244, WO 04/080962, WO04/111042, WO05/092897, WO06/029799, WO07/080066, WO07/096058, WO09/019005, WO09/019015, WO09/049851, WO 10/069834, WO10/000773, WO10/057880, WO10/081894, WO10/089210, WO10/102848 and WO10/133232). Compounds having similar substitutions are also known; 3-hydroxy-5,5-dimethyl-2-phenylcyclopent-2-en-1-one from the publication Micklefield et al., Tetrahedron, (1992), 7519-26 and also the natural compound involutin (-)-cis-5-(3,4-dihydroxyphenyl)-3,4-dihydroxy-2-(4-hydroxyphenyl)cyclopent-2-enone from the publication Edwards et al., J. Chem. Soc. S, (1967), 405-9. An insecticidal or acaricidal action is not described. Moreover, 2-(2,4,6-trimethylphenyl)-1,3-indanedione is known from the publication J. Economic Entomology, 66, (1973), 584 and the laid-open application DE-A 2 361 084, with herbicidal and acaricidal activities being stated.

It is known that certain substituted 2-arylcyclohexanediones have herbicidal, insecticidal and acaricidal properties (U.S. Pat. Nos. 4,175,135, 4,256,657, 4,256,658, 4,256,659, 4,257,858, 4,283,348, 4,303,669, 4,351,666, 4,409,153, 4,436,666, 4,526,723, 4,613,17, 4,659,372, DE-A 2 813 341, and also Wheeler, T. N., J. Org. Chem. 44, 4906 (1979)), WO 99/43649, WO 99/48869, WO 99/55673, WO 01/17972, WO 01/74770, WO 03/013249, WO 04/080 962, WO 04/111 042, WO 05/092897, WO 06/029799, WO 07/096,058, WO 08/071405, WO 08/110307, WO 08/110308, WO 09/074314, WO 08/145336, WO 09/015887, WO09/074314, WO10/046194, WO10/081755 and WO10/089211).

It is known that certain substituted 4-arylpyrazolidine-3,5-diones have acaricidal, insecticidal and herbicidal properties (cf., for example, WO 92/16 510, EP-A-508 126, WO 96/11 574, WO 96/21 652, WO 99/47525, WO 01/17 351, WO 01/17 352, WO 01/17 353, WO 01/17 972, WO 01/17 973, WO 03/028 466, WO 03/062 244, WO 04/080 962, WO 04/111 042, WO 05/005428, WO 05/016873, WO 05/092897, WO 06/029799 and WO 07/096,058).

It is known that certain tetrahydropyridones have herbicidal properties (JP 0832530). Specific 4-hydroxytetrahydropyridones having acaricidal, insecticidal and herbicidal properties are also known (JP 11152273). Furthermore, 4-hydroxytetrahydropyridones have been disclosed as pesticides and herbicides in WO 01/79204 and WO 07/096,058. 4-Hydroxyquinolones are disclosed in WO 03/01045.

It is known that certain 5,6-dihydropyrone derivatives as protease inhibitors have antiviral properties (WO 95/14012). Furthermore, 4-phenyl-6-(2-phenethyl)-5,6-dihydropyrone is known from the synthesis of kawalactone derivatives (Kappe et al., Arch. Pharm. 309, 558-564 (1976)). Moreover, 5,6-dihydropyrone derivatives are known as intermediates (White, J. D., Brenner, J. B., Deinsdale, M. J., J. Amer. Chem. Soc. 93, 281-282 (1971)). 3-Phenyl-5,6-dihydropyrone derivatives with applications in crop protection are described in WO 01/98288 and WO 07/09658.

4'-Biphenyl-substituted tetronic acid derivatives for the therapy of viral disorders are disclosed in WO 2008/022725.

WO 2005/089118 and WO2007/039286 disclose, in a general manner, nitrogenous bicyclic structures for therapy, 5'-biphenyl-substituted cyclic ketoenols not being specifically mentioned.

4-Phenyl-substituted [1.2]-oxazine-3,5-diones as herbicides were initially described in WO 01/17972. Furthermore, 4-acyl-substituted [1.2]-oxazine-3,5-diones as pesticides, but especially as herbicides and growth regulators, are described, for example, in EP-A-39 48 89; WO 92/07837, U.S. Pat. No. 5,728,831, and as herbicides and pesticides in WO 03/048138.

Compound A is specifically disclosed in WO2008/067910 (Table 1, page 26, line 4). WO2008/067910 does not disclose the suitability of compound A for therapeutic purposes.

The present application establishes the priority for the therapeutic use of compound A. At the same time as the present priority-establishing application, the subject-matter of which is the therapeutic use of compound A alone, a PCT application, inter alia, was filed, the subject-matter of which is the therapeutic use of numerous cyclic ketoenols and which claims the priority of a German application having the application number DE102010008644.4. Compound A is example 1-118 in the PCT application, but is not part of DE102010008644.4.

The structurally closest prior art may be Example I-1-a-16 of WO99/48869 which differs from compound A only by a missing fluorine atom at the outer phenyl ring of the biphenyl. The therapeutic use of Example I-1-a-16 of WO99/48869 also forms part of the subject-matter of DE102010008644.4 and the PCT application which claims the priority of DE102010008644.4 (Example 1-2).

However, the structurally closest prior art may also be Example I-1-a-31 of WO03/059065 which differs from compound A in that a fluorine atom at the outer phenyl ring of the biphenyl is replaced by a chlorine atom. The therapeutic use of Example I-1-a-31 of WO03/059065 also forms part of the subject-matter of DE102010008644.4 and the PCT application which claims the priority of DE102010008644.4 (Example 1-81).

Based on this prior art, it was an object of the present invention to provide a particularly effective structure for the therapy of disorders.

The structure according to the invention should be suitable in particular for the prophylaxis and therapy of tumour disorders and have advantages compared to the structures known from the prior art.

Surprisingly, it has now been found that the compound A

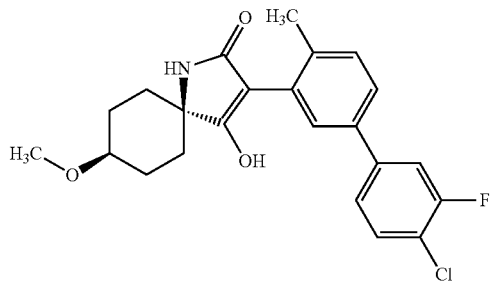 [SMILES: CO[C@H]1CC[C@]2(CC1)NC(=O)C(c1cc(-c3ccc(Cl)c(F)c3)ccc1C)=C2O]

is particularly suitable for the therapy of disorders.

Here, it was unforeseeable whether and which of the structures known as insecticides or herbicides would achieve the object of the invention to greatest effect, that is to say to provide a structure which can be used to greatest effect in the therapy of human disorders.

Compound A has comparable enzyme inhibition data to Example I-1-a-16 of WO99/48869 which may be considered as the structurally closest prior art. However, surprisingly, compound A is distinguished by a broader therapeutic window in the MCF7 zenograft model then this prior art, which is ineffective in this model at tolerated doses.

Compound A has better enzyme inhibition data than Example I-1-a-31 of WO03/059065 which may likewise be considered as the structurally closest prior art.

From the large group of the cyclic ketoenols known as insecticides, fungicides or herbicides, compound A is, surprisingly distinguished by better enzyme inhibition and/or better in vivo efficacy at tolerated doses.

The present invention likewise embraces the use of the physiologically acceptable salts of compound A.

Physiologically acceptable salts of compound A also include salts of conventional bases, such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

The present invention furthermore provides medicaments comprising compound A and at least one or more active compounds, in particular for the prophylaxis and/or therapy of tumour disorders.

Compound A can act systemically and/or locally. For this purpose, they can be administered in a suitable manner, such as, for example, orally, parenterally, pulmonarily, nasally, sublingually, lingually, buccally, rectally, dermally, transdermally, conjunctivally, otically, as or as an implant or stent.

For these administration routes, compound A can be administered in suitable administration forms.

Suitable for oral administration are administration forms working according to the prior art, which release compound A rapidly and/or in modified form and comprise compound A in crystalline and/or amorphized and/or dissolved form, such as, for example, tablets (non-coated or coated tablets, for example coated with enteric, slowly dissolving or insoluble coats which control the release of the compound according to the invention), tablets which decompose rapidly in the oral cavity or films/wafers, films/lyophylizates, capsules (for example hard gelatin capsules or soft gelatin capsules), sugar-coated tablets, granules, pellets, powders, emulsions, suspensions, aerosols or solutions.

Parenteral administration can take place with circumvention of an absorption step (for example intravenous, intraarterial, intracardiac, intraspinal or intralumbar) or with involvement of an absorption (for example intramuscular, subcutaneous, intracutaneous, percutaneous or intraperitoneal). For parenteral administration, suitable administration forms are, inter alia, injection and infusion preparations in the form of solutions, suspensions, emulsions, lyophilizates or sterile powders.

Suitable for the other administration routes are, for example, pharmaceutical forms for inhalation (inter alia powder inhalers, nebulizers), nasal drops, nasal solutions, nasal sprays; tablets, films/wafers or capsules to be applied lingually, sublingually or buccally, suppositories, ear or eye preparations, vaginal capsules, aqueous suspensions (lotions, shake lotions), lipophilic suspensions, ointments, creams, transdermal therapeutic systems (such as, for example, patches), milk, pastes, foams, dusting powders, implants or stents.

Compound A can be converted into the administration forms mentioned. This may take place in a manner known per se by mixing with inert non-toxic, pharmaceutically acceptable auxiliaries. These auxiliaries include, inter alia, carriers (for example microcrystalline cellulose, lactose, mannitol), solvents (for example liquid polyethylene glycols), emulsifiers and dispersants or wetting agents (for example sodium dodecylsulphate, polyoxysorbitan oleate), binders (for example polyvinylpyrrolidone), synthetic and natural polymers (for example albumin), stabilizers (e.g. antioxidants such as, for example, ascorbic acid), colorants (e.g. inorganic pigments such as, for example, iron oxides) and taste and/or odour corrigents.

The present invention furthermore provides medicaments comprising compound A, usually together with one or more inert non-toxic, pharmaceutically suitable auxiliaries, and their use for the purposes mentioned above.

Formulation of compound A to give pharmaceutical products takes place in a manner known per se by converting the active ingredient(s) with the excipients customary in pharmaceutical technology into the desired administration form.

Excipients which can be employed in this connection are, for example, carrier substances, fillers, disintegrants, binders, humectants, lubricants, absorbents and adsorbents, diluents, solvents, cosolvents, emulsifiers, solubilizers, masking flavours, colorants, preservatives, stabilizers, wetting agents, salts to alter the osmotic pressure or buffers.

Reference should be made in this connection to Remington's Pharmaceutical Science, 15th ed. Mack Publishing Company, East Pennsylvania (1980).

The pharmaceutical formulations may be
in solid form, for example as tablets, coated tablets, pills, suppositories, capsules, transdermal systems or
in semisolid form, for example as ointments, creams, gels, suppositories, emulsions or
in liquid form, for example as solutions, tinctures, suspensions or emulsions.

Excipients in the context of the invention may be, for example, salts, saccharides (mono-, di-, tri-, oligo-, and/or polysaccharides), proteins, amino acids, peptides, fats, waxes, oils, hydrocarbons and derivatives thereof, where the excipients may be of natural origin or may be obtained by synthesis or partial synthesis.

Suitable for oral or peroral administration are in particular tablets, coated tablets, capsules, pills, powders, granules, pastilles, suspensions, emulsions or solutions. Suitable for parenteral administration are in particular suspensions, emulsions and especially solutions.

The present invention relates to the use of compound A for the prophylaxis and therapy of human disorders, in particular of tumour disorders.

Compound A can be used in particular for inhibiting or reducing cell proliferation and/or cell division and/or to induce apoptosis.

Compound A is suitable in particular for the prophylaxis and/or therapy of hyper-proliferative disorders such as, for example,
- psoriasis,
- keloids and other skin hyperplasias,
- benign prostate hyperplasias (BPH),
- solid tumours and
- haematological tumours.

Solid tumour which can be treated in accordance with the invention are, for example, tumours of the breast, the respiratory tract, the brain, the reproductive organs, the gastrointestinal tract, the urogenital tract, the eye, the liver, the skin, the head and the neck, the thyroid gland, the parathyroid gland, the bones and the connective tissue and metastases of these tumours.

Haematological tumours which can be treated are, for example,
- multiple myelomas,
- lymphomas or
- leukaemias.

Breast tumours which can be treated are, for example:
- breast carcinomas with positive hormone receptor status
- breast carcinomas mit negative hormone receptor status
- Her-2 positive breast carcinomas
- hormone receptor and Her-2 negative breast carcinomas
- BRCA-associated breast carcinomas
- inflammatory breast carcinomas.

Tumours of the respiratory tract which can be treated are, for example,
- non-small-cell bronchial carcinomas and
- small-cell bronchial carcinomas.

Tumours of the brain which can be treated are, for example,
- gliomas,
- glioblastomas,
- astrocytomas,
- meningiomas and
- medulloblastomas.

Tumours of the male reproductive organs which can be treated are, for example:
- prostate carcinomas,
- malignant testicular tumours and
- penis carcinomas.

Tumours of the female reproductive organs which can be treated are, for example:
- endometrial carcinomas
- cervix carcinomas
- ovarial carcinomas
- vaginal carcinomas
- vulvar carcinomas Tumours of the gastrointestinal tract which can be treated are, for example:
- colorectal carcinomas
- anal carcinomas
- stomach carcinomas
- pancreas carcinomas
- oesophagus carcinomas
- gall bladder carcinomas
- carcinomas of the small intestine
- salivary gland carcinomas
- neuroendocrine tumours
- gastrointestinal stroma tumours Tumours of the urogenital tract which can be treated are, for example:
- urinary bladder carcinoma
- kidney cell carcinoma
- carcinomas of the renal pelvis and lower urinary tract Tumours of the eye which can be treated are, for example:
- retinoblastomas
- intraocular melanomas Tumours of the liver which can be treated are, for example:
- hepatocellular carcinomas
- cholangiocellular carcinomas Tumours of the skin which can be treated are, for example:
- malignant melanomas
- basaliomas
- spinaliomas
- Kaposi sarcomas
- Merkel cell carcinomas Tumours of the head and neck which can be treated are, for example:
- larynx carcinomas
- carcinomas of the pharynx and the oral cavity Sarcomas which can be treated are, for example:
- soft tissue sarcomas
- osteosarcomas Lymphomas which can be treated are, for example:
- non-Hodgkin lymphomas
- Hodgkin lymphomas
- cutaneous lymphomas
- lymphomas of the central nervous system
- AIDS-associated lymphomas Leukaemias which can be treated are, for example:
- acute myeloid leukaemias
- chronic myeloid leukaemias
- acute lymphatic leukaemias
- chronic lymphatic leukaemias
- hairy cell leukaemias Advantageously, compound A can be used for the prophylaxis and/or therapy of:
breast carcinomas, in particular hormone receptor-negative, hormone receptor-positive or BRCA-associated breast carcinomas, and also
pancreas carcinomas, renal cell carcinomas, hepatocellular carcinomas, malignant melanomas and other skin tumours, non-small cell bronchial carcinomas, endometrial carcinomas, colorectal carcinomas, stomach carcinomas and prostate carcinomas.

Particularly advantageously, compound A can be used for the prophylaxis and/or therapy of:
breast carcinomas, in particular hormone receptor-negative and hormone receptor-positive, and also
pancreas carcinomas, non-small cell bronchial carcinomas, endometrial carcinomas, colorectal carcinomas, stomach carcinomas and prostate carcinomas.

These disorders are well-characterized in man, but also exist in other mammals.

The present application further provides compound A for use as a medicament in particular for the prophylaxis and/or therapy of tumour disorders.

The present application furthermore provides compound A for the prophylaxis and/or therapy of breast carcinomas, pancreas carcinomas, renal cell carcinomas, hepatocellular carcinomas, malignant melanomas and other skin tumours, non-small cell bronchial carcinomas, endometrial carcinomas, colorectal carcinomas, stomach carcinomas or prostate carcinomas.

The present application advantageously provides compound A for the prophylaxis and/or therapy of breast carcinomas, in particular hormone receptor-negative and hormone receptor-positive, and also pancreas carcinomas, non-small cell bronchial carcinomas, endometrial carcinomas, colorectal carcinomas, stomach carcinomas and prostate carcinomas.

The invention furthermore provides the use of compound A for preparing a medicament.

The present application furthermore provides the use of the compound for preparing a medicament for the prophylaxis and/or therapy of tumour disorders.

The present application furthermore provides the use of compound A for preparing a medicament for the prophylaxis and/or therapy of breast carcinomas, pancreas carcinomas, renal cell carcinomas, hepatocellular carcinomas, malignant melanomas and other skin tumours, non-small cell bronchial carcinomas, endometrial carcinomas, colorectal carcinomas, stomach carcinomas or prostate carcinomas.

The present application advantageously provides the use of compound A for preparing a medicament for the prophylaxis and/or therapy of breast carcinomas, in particular hormone receptor-negative and hormone receptor-positive, and also pancreas carcinomas, non-small cell bronchial carcinomas, endometrial carcinomas, colorectal carcinomas, stomach carcinomas and prostate carcinomas.

The present application furthermore provides the use of the compound for the prophylaxis and/or therapy of tumour disorders.

The present application furthermore provides the use of compound A for the prophylaxis and/or therapy of breast carcinomas, pancreas carcinomas, renal cell carcinomas, hepatocellular carcinomas, malignant melanomas and other skin tumours, non-small cell bronchial carcinomas, endometrial carcinomas, colorectal carcinomas, stomach carcinomas or prostate carcinomas.

The present application advantageously provides the use of compound A for the prophylaxis and/or therapy of breast carcinomas, in particular hormone receptor-negative and hormone receptor-positive, and also pancreas carcinomas, non-small cell bronchial carcinomas, endometrial carcinomas, colorectal carcinomas, stomach carcinomas and prostate carcinomas.

The present application furthermore provides pharmaceutical formulations in the form of tablets comprising compound A for the prophylaxis and/or therapy of breast carcinomas, pancreas carcinomas, renal cell carcinomas, hepatocellular carcinomas, malignant melanomas and other skin tumours, non-small cell bronchial carcinomas, endometrial carcinomas, colorectal carcinomas, stomach carcinomas or prostate carcinomas.

The present application advantageously provides pharmaceutical formulations in the form of tablets comprising compound A for the prophylaxis and/or therapy of breast carcinomas, in particular hormone receptor-negative and hormone receptor-positive, and also pancreas carcinomas, non-small cell bronchial carcinomas, endometrial carcinomas, colorectal carcinomas, stomach carcinomas and prostate carcinomas.

The invention furthermore provides the use of compound A for treating disorders associated with proliferative processes.

Compound A can be employed by themselves or, if required, in combination with one or more other pharmacologically active substances, as long as this combination does not lead to unwanted and unacceptable side effects. Accordingly, the present invention furthermore provides medicaments comprising compound A and one or more further active compounds, in particular for prophylaxis and/or therapy of the abovementioned diseases.

For example, compound A can be combined with known antihyperproliferative, cytostatic or cytotoxic substances for treatment of cancer disorders. The combination of compound A with other substances customary for cancer therapy or else with radiotherapy is indicated in particular.

Suitable active compounds for combinations which may be mentioned by way of example are:
afinitor, aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BCG or tice-BCG, bestatin, beta-methasone acetate, betamethasone sodium phosphate, bexarotene, bleomycin sulphate, broxuridine, bortezomib, busulfan, calcitonin, campath, capecitabine, carboplatin, casodex, cefesone, celmoleukin, cerubidin, chlorambucil, cisplatin, cladribin, clodronic acid, cyclophosphamide, cytarabine, dacarbazine, dactinomycin, daunoxome, decadron, decadron phosphate, delestrogen, denileukin diftitox, depomedrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin-alfa, epogen, eptaplatin, ergamisol, estrace, estradiol, estramustine sodium phosphate, ethynylestradiol, ethyol, etidronic acid, etopophos, etoposide, fadrozole, farstone, filgrastim, finasteride, fligrastim, floxuridine, fluconazole, fludarabin, 5-fluorodeoxyuridine monophosphate, 5-fluoruracil (5-FU), fluoxymesterone, flutamide, formestane, fosteabine, fotemustine, fulvestrant, gammagard, gemcitabine, gemtuzumab, gleevec, gliadel, goserelin, granisetron hydrochloride, histrelin, hycamtin, hydrocortone, erythro-hydroxynonyladenine, hydroxyurea, ibritumomab tiuxetan, idarubicin, ifosfamide, interferon-alpha, interferon-alpha-2, interferon-alpha-2α, interferon-alpha-2β, interferon-alpha-nl, interferon-alpha-n3, interferon-beta, interferon-gamma-1α, interleukin-2, intron A, iressa, irinotecan, kytril, lapatinib, lentinan sulphate, letrozole, leucovorin, leuprolide, leuprolide acetate, levamisole, levofolic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, mesna, methotrexate, metvix, miltefosine, minocycline, mitomycin C, mitotane, mitoxantrone, modrenal, myocet, nedaplatin, neulasta, neumega, neupogen, nilutamide, nolvadex, NSC-631570, OCT-43, octreotide, ondansetron hydrochloride, orapred, oxaliplatin, paclitaxel, pediapred, pegaspargase, pegasys, pentostatin, picibanil, pilocarpine hydrochloride, pirarubicin, plicamycin, porfimer sodium, prednimustine, prednisolone, prednisone, premarin, procarbazine, procrit, raltitrexed, RDEA119, rebif, rhenium-186 etidronate, rituximab, roferon-A, romurtide, salagen, sandostatin, sargramostim, semustine, sizofiran, sobuzoxane, solumedrol, streptozocin, strontium-89 chloride, synthroid, tamoxifen, tamsulosin, tasonermin, tastolactone, taxoter, teceleukin, temozolomide, teniposide, testosterone propionate, testred, thioguanine, thiotepa, thyrotropin, tiludronic acid, topotecan, toremifen, tositumomab, tastuzumab, treosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin-stimalamer, zofran; ABI-007, acolbifen, actimmune, affinitak, aminopterin, arzoxifen, asoprisnil, atamestane, atrasentan, BAY 43-9006 (sorafenib), avastin, CCI-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon-gamma, intron-PEG, ixabepilone, keyhole limpet hemocyanine, L-651582, lanreotide, lasofoxifen, libra, lonafarnib, miproxifen, minodronate, MS-209, liposomal MTP-PE, MX-6, nafarelin, nemorubicin, neovastat, nolatrexed, oblimersen, onko-TCS, osidem, paclitaxel polyglutamate, pamidronate disodium, PN-401, QS-21, quazepam, R-1549, raloxifen, ranpirnas, 13-cis-retinoic acid, satraplatin, seocalcitol, T-138067, tarceva, taxoprexin, thymosin-alpha-1, tiazofurin, tipifarnib, tirapazamine, TLK-286, toremifen, transMID-107R, valspodar, vapreotide, vatalanib, verteporfin, vinflunin, Z-100, zoledronic acid and combinations of these.

In a preferred embodiment, compound A can be combined with antihyperproliferative agents, which can be, by way of example—without this list being conclusive:
aminoglutethimide, L-asparaginase, azathioprine, 5-azacytidine, bleomycin, busulfan, carboplatin, carmustine, chlorambucil, cisplatin, colaspase, cyclophosphamide, cytarabine, dacarbazine, dactinomycin, daunorubicin, diethylstilbestrol, 2',2'-difluorodeoxycytidine, docetaxel, doxorubicin (adriamycin), epirubicin, epothilone and its derivatives, erythro-hydroxynonyladenin, ethynyl-estradiol, etoposide, fludarabin phosphate, 5-fluorodeoxyuridine, 5-fluorodeoxyuridine mono-phosphate, 5-fluorouracil, fluoxymesterone, flutamide, hexamethylmelamine, hydroxyurea, hydroxyprogesterone caproate, idarubicin, ifosfamide, interferon, irinotecan, leucovorin, lomustine, mechlorethamine, medroxyprogesterone acetate, megestrol acetate, melphalan, 6-mercaptopurine, mesna, methotrexate, mitomycin C, mitotane, mitoxantrone, paclitaxel, pentostatin, N-phosphono-acetyl L-aspartate (PALA), plicamycin, prednisolone, prednisone, procarbazine, raloxifen, semustine, streptozocin, tamoxifen, teniposide, testosterone propionate, thioguanine, thiotepa, topotecan, trimethylmelamine, uridine, vinblastine, vincristine, vindesine and vinorelbine.

Compound A can also be combined in a very promising manner with biological therapeutics, such as antibodies (e.g. avastin, rituxan, erbitux, herceptin) and recombinant proteins.

Compound A may also achieve positive effects in combination with other therapies directed against angiogenesis, such as, for example, with avastin, axitinib, regorafenib, recentin, sorafenib or sunitinib. Combinations with inhibitors of the proteasome and of mTOR and antihormones and steroidal metabolic enzyme inhibitors are particularly suitable because of their favourable profile of side effects.

Generally, the following aims can be pursued with the combination of compound A with other agents having a cytostatic or cytotoxic action:
an improved activity in slowing down the growth of a tumour, in reducing its size or even in its complete elimination compared with treatment with an individual active compound;
the possibility of employing the chemotherapeutics used in a lower dosage than in monotherapy;
the possibility of a more tolerable therapy with few side effects compared with individual administration;
the possibility of treatment of a broader spectrum of tumour diseases;
achievement of a higher rate of response to the therapy;
a longer survival time of the patient compared with present-day standard therapy.

Compound A can moreover also be employed in combination with radiotherapy and/or surgical intervention.

EXPERIMENTAL PART

1. Comparative Examples

Table V shows Example I-1-a-16 of WO99/488691 and Example I-1-a-31 of WO03/059065, which the Applicant considers to be the closest prior art.

TABLE V

| Ex. | Structure/Name | disclosed in | Analysis<br>$^1$H-NMR: δ [ppm]<br>retention time,<br>[M + H]$^+$, Method |
|---|---|---|---|
| C.1 | 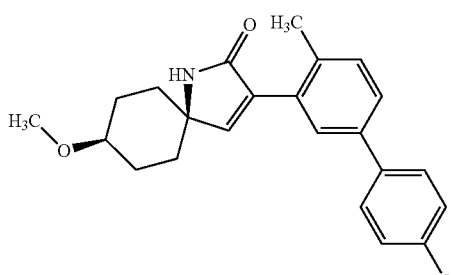<br>(5s,8s)-3-(4'-chloro-4-methylbiphenyl-3-yl)-4-hydroxy-8-methoxy-1-azaspiro[4.5]dec-3-en-2-one | WO 99/48869<br>I-1-a-16 | (300 MHz, DMSO-d$_6$):<br>1.39-1.62 (m, 4H), 1.84-2.05 (m, 4H), 2.18 (s, 3H), 3.07-3.20 (m, 1H), 3.26 (s, 3H), 7.30 (d, 1H), 7.34 (d, 1H), 7.45-7.53 (m, 3H), 7.62-7.68 (m, 2H), 8.18 (br. s, 1H), 10.82 (br. s, 1H).<br>1.20 min, 398, Method 1 |

| Ex. | Structure/Name | disclosed in | Analysis<br>¹H-NMR: δ [ppm]<br>retention time,<br>[M + H]⁺, Method |
|---|---|---|---|
| C.2 | ![structure] 3-(3',4'-dichloro-4-methylbiphenyl-3-yl)-4-hydroxy-8-methoxy-1-azaspiro[4.5]dec-3-en-2-one | WO 03/059065<br>I-1-a-31 | |

LC-MS and HPLC Methods

Method 1 (UPLC-MS)

Instrument: Waters Acquity UPLC-MS SQD 3001; column: Acquity UPLC BEH C18 1.7 50×2.1 mm; mobile phase A: water+0.1% formic acid, mobile phase B: acetonitrile; gradient: 0-1.6 min 1-99% B, 1.6-2.0 min 99% B; flow rate 0.8 ml/min; temperature: 60° C.; injection: 2 µl; DAD scan: 210-400 nM.

Method 2 (UPLC-MS)

Instrument: Waters Acquity UPLC-MS ZQ4000; column: Acquity UPLC BEH C18 1.7 50×2.1 mm; mobile phase A: water+0.05% formic acid, mobile phase B: acetonitrile+ 0.05% formic acid; gradient: 0-1.6 min 1-99% B, 1.6-2.0 min 99% B; flow rate 0.8 ml/min; temperature: 60° C.; injection: 2 µl; DAD scan: 210-400 nM.

Method 3 (UPLC-MS):

Instrument: Waters Acquity UPLC-MS SQD 3001; column: Acquity UPLC BEH C18 1.7 50×2.1 mm; mobile phase A: water+0.1% formic acid, mobile phase B: acetonitrile; gradient: 0-1.6 min 1-99% B, 1.6-2.0 min 99% B; flow rate 0.8 ml/min; temperature: 60° C.; injection: 2 µl; DAD scan: 210-400 nm.

Preparation of Comparative Example C.1 a) Intermediates

Intermediate C.1.1

(4'-chloro-4-methylbiphenyl-3-yl)acetyl chloride

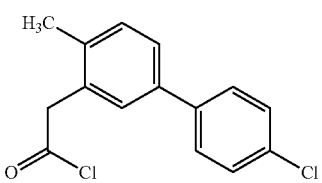 [SMILES: Cc1ccc(-c2ccc(Cl)cc2)cc1CC(=O)Cl]

5.00 g (19.18 mmol) (4'-chloro-4-methylbiphenyl-3-yl) acetic acid (EP 2029531 A1 and US 2009/298828 A1) were dissolved in 36.51 g (306.84 mmol) of thionyl chloride. The reaction mixture was stirred at 80° C. for four hours and then concentrated under reduced pressure. Drying under fine vacuum gave 5.4 g (100% of theory) of the title compound as a brownish oil.

¹H-NMR (300 MHz, CDCl₃): δ [ppm]=2.36 (s, 3H), 4.22 (s, 2H), 7.29 (d, 1H), 7.35-7.55 (m, 6H).

Intermediate C.1.2

Methyl-cis-1-{[(4'-chloro-4-methylbiphenyl-3-yl) acetyl]amino}-4-methoxycyclohexane-carboxylate

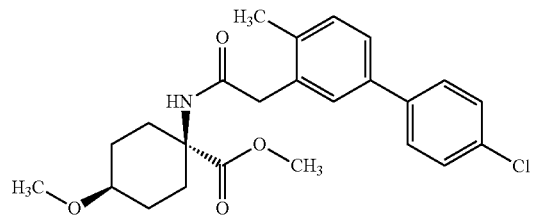 [SMILES: COC(=O)[C@]1(NC(=O)Cc2cc(-c3ccc(Cl)cc3)ccc2C)CC[C@@H](OC)CC1]

At room temperature, 5.41 g (24.2 mmol) of methyl-cis-1-amino-4-methoxycyclohexanecarboxylate hydrochloride (EP 1791816 A1 and WO 2006/29799 A1), 14.8 mg (1.21 mmol) of DMAP and 8.4 ml (60 5 mmol) of triethylamine were, under nitrogen, dissolved in 118 ml of dichloromethane. A solution of 6.75 g (24.2 mmol) of intermediate C.1.1 in 60 ml of dichloromethane was then added dropwise. The resulting reaction mixture was stirred at room temperature overnight. For work-up, the mixture was diluted with dichloromethane and the organic phase was washed with aqueous saturated sodium bicarbonate solution and aqueous 5% strength citric acid. The organic phase was dried over sodium sulphate and then filtered and concentrated. This gave 10.9 g of the title compound which were purified further by chromatography on silica gel (mobile phase: hexane/ethyl acetate gradient).

¹H-NMR (300 MHz, DMSO-d₆): δ [ppm]=1.31-1.47 (m, 2H), 1.60-1.73 (m, 2H), 1.75-1.86 (m, 2H), 2.00-2.11 (m, 2H), 2.27 (s, 3H), 3.09-3.20 (m, 1H), 3.21 (s, 3H), 3.51 (s, 3H), 3.58 (s, 2H), 7.23 (d, 1H), 7.43 (dd, 1H), 7.46-7.54 (m, 3H), 7.61-7.68 (m, 2H), 8.31 (s, 1H).

LC-MS (method 1): R_t=1.38 min; MS (ESIpos): m/z=430 [M+H]⁺.

b) End Product C.1

(5s,8s)-3-(4'-chloro-4-methylbiphenyl-3-yl)-4-hydroxy-8-methoxy-1-azaspiro[4.5]dec-3-en-2-one

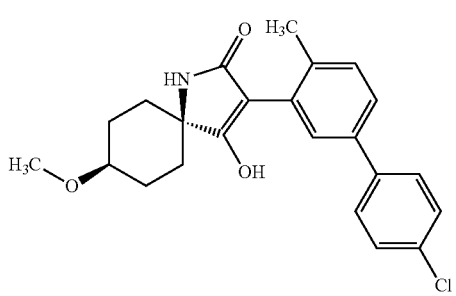 [SMILES: CO[C@H]1CC[C@]2(CC1)NC(=O)C(c1cc(-c3ccc(Cl)cc3)ccc1C)=C2O]

At room temperature and under nitrogen, 4.63 g (41 3 mmol) of potassium tert-butoxide were added to 8.87 g (20.6 mmol) of intermediate C.1.2 in 103 ml of N,N-dimethylformamide. The reaction mixture was stirred at 80° C. for 60 minutes. For work-up, the cooled reaction mixture was poured into 1 l of ice water, adjusted to pH 3 using 1N aqueous hydrogen chloride solution and stirred for three hours, and the precipitate was filtered off with suction, washed with water and dried. The crude product was purified further by stirring with diethyl ether overnight, filtration and drying. This gave 7.75 g (95% of theory) of the title compound.

$^1$H-NMR (300 MHz, DMSO-$d_6$): δ [ppm]=1.39-1.62 (m, 4H), 1.84-2.05 (m, 4H), 2.18 (s, 3H), 3.07-3.20 (m, 1H), 3.26 (s, 3H), 7.30 (d, 1H), 7.34 (d, 1H), 7.45-7.53 (m, 3H), 7.62-7.68 (m, 2H), 8.18 (br. s, 1H), 10.82 (br. s, 1H).

LC-MS (method 3): $R_t$=1.19 min; MS (ESIpos): m/z=398 [M+H]$^+$.

Comparative Example C.2

Comparative Example C.2 is Example I-1-a-31 of WO03/059065.

The therapeutic use of Example I-1-a-31 of WO03/059065 also forms part of the subject-matter of DE102010008644.4 and the PCT application which claims the priority of DE102010008644.4 (Example 1-81).

2. Compound A

Preparation of Compound A a) Intermediates

Intermediate A.1

(4'-chloro-3'-fluoro-4-methylbiphenyl-3-yl)acetic acid

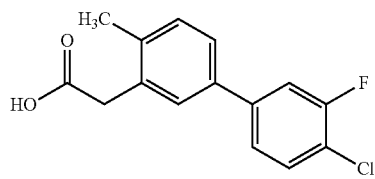 [SMILES: Cc1ccc(-c2ccc(Cl)c(F)c2)cc1CC(=O)O]

Under argon, 33.5 g (192 mmol) (4-chloro-3-fluorophenyl)boronic acid were added to a solution of 40.0 g (175 mmol) of (5-bromo-2-methylphenyl)acetic acid (EP 1791816 and WO 2006/29799) in a mixture of 437 ml (437 mmol) of degassed 1N aqueous sodium hydroxide solution, 160 ml of degassed water and 160 ml of degassed tetrahydrofuran. The mixture was stirred for 10 minutes, 507 mg (1.75 mmol) of tri-tert-butylphosphonium tetrafluoroborate and 532 mg (1.75 mmol) of palladium(II) acetylacetonate were added and the mixture was stirred at room temperature for 20 h. Toluene and water were then added, the pH was adjusted to 1-2 using concentrated aqueous hydrogen chloride solution, the mixture was stirred for 10 minutes, the phases were separated, the aqueous phase was extracted twice with toluene and the combined organic phases were dried over sodium sulphate, filtered and concentrated. The residue was stirred in 300 ml of a 6/1 mixture of n-hexane/tert-butyl methyl ether for 30 minutes, filtered off with suction, washed with n-hexane and dried under reduced pressure. This gave 38.0 g (78% of theory) of the title compound.

$^1$H-NMR (300 MHz, DMSO-$d_6$): δ [ppm]=2.27 (s, 3H), 3.67 (s, 2H), 7.27 (d, 1H), 7.49-7.59 (m, 3H), 7.61-7.75 (m, 2H), 12.4 (s, 1H).

LC-MS (method 1): $R_t$=1.31 min; MS (ESIneg): m/z=277 [M+H]$^+$.

Intermediate A.2

Methyl-cis-1-{[(4'-chloro-3'-fluoro-4-methylbiphenyl-3-yl)acetyl]amino}-4-methoxycyclohexane-carboxylate

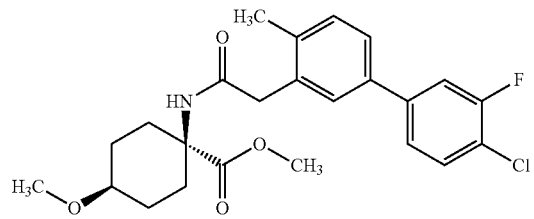 [SMILES: COC(=O)[C@]1(NC(=O)Cc2cc(-c3ccc(Cl)c(F)c3)ccc2C)CC[C@@H](OC)CC1]

10.0 g (35.9 mmol) of intermediate A.1 were dissolved in 14.9 ml (205 mmol) of thionyl chloride. The reaction mixture was stirred at 90° C. for 1 h and then concentrated. This gave 10.8 g (100% of theory) of (4'-chloro-3'-fluoro-4-methylbiphenyl-3-yl)acetyl chloride. 10.6 g (35 7 mmol) of (4'-chloro-3'-fluoro-4-methylbiphenyl-3-yl)acetyl chloride were dissolved in 120 ml of acetonitrile. 12.0 g (53.7 mmol) of methyl-cis-1-amino-4-methoxycyclohexanecarboxylate hydrochloride (described in EP 1791816 and WO 2006/29799) were taken up in ethyl acetate, and saturated aqueous sodium bicarbonate solution was added. The phases were separated and the aqueous phase was extracted twice with ethyl acetate. The combined organic phases were dried over sodium sulphate, filtered and concentrated. This gave 8.50 g of methyl-cis-1-amino-4-methoxy-cyclohexanecarboxylate. 17.3 g (125 mmol) of potassium carbonate were added to 8.02 g (42.8 mmol) of methyl-cis-1-amino-4-methoxycyclohexanecarboxylate in 120 ml of acetonitrile. With ice-cooling, the solution of the acid chloride was added dropwise and the mixture was stirred at room temperature overnight. The mixture was then concentrated, water was added to the residue, the mixture was extracted with dichloromethane and the combined organic phases were washed with 1N aqueous hydrogen chloride solution and saturated aqueous sodium bicarbonate solution, dried over sodium sulphate, filtered and concentrated. This gave 15.7 g (98% of theory) of the title compound which were reacted without further purification.

$^1$H-NMR (300 MHz, DMSO-$d_6$): δ [ppm]=1.30-1.47 (m, 2H), 1.60-1.74 (m, 2H), 1.75-1.85 (m, 2H), 1.99-2.11 (m, 2H), 2.28 (s, 3H), 3.09-3.20 (m, 1H), 3.21 (s, 3H), 3.52 (s, 3H), 3.58 (s, 2H), 7.24 (d, 1H), 7.46-7.55 (m, 2H), 7.57 (d, 1H), 7.61-7.72 (m, 2H), 8.30 (s, 1H).

LC-MS (method 2): $R_t$=1.36 min; MS (ESIpos): m/z=448 [M+H]$^+$.

b) End Product Compound A (5s,8s)-3-(4'-chloro-3'-fluoro-4-methylbiphenyl-3-yl)-4-hydroxy-8-methoxy-1-azaspiro[4.5]dec-3-en-2-one

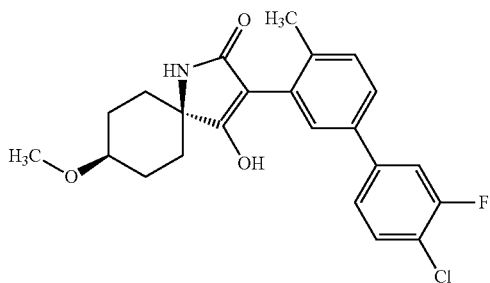 [SMILES: CO[C@H]1CC[C@]2(CC1)NC(=O)C(c1cc(-c3ccc(Cl)c(F)c3)ccc1C)=C2O]

Under nitrogen, 4.32 g (38.5 mmol) of potassium tert-butoxide were added to 15.7 g (35 0 mmol) of intermediate A.2 in 60 ml of N,N-dimethylformamide. The reaction mixture was stirred at room temperature for 20 minutes. The reaction mixture was then added to ice water, 160 ml of 1N aqueous hydrogen chloride solution were added dropwise, the mixture was stirred for 30 minutes and the precipitate was filtered off with suction, washed with water and dried. This gave 14.2 g (97% of theory) of the title compound.

$^1$H-NMR (300 MHz, DMSO-$d_6$): δ [ppm]=1.40-1.62 (m, 4H), 1.85-2.04 (m, 4H), 2.19 (s, 3H), 3.07-3.20 (m, 1H), 3.27 (s, 3H), 7.31 (d, 1H), 7.39 (d, 1H), 7.48-7.57 (m, 2H), 7.60-7.73 (m, 2H), 8.20 (s, 1H), 10.82 (s, 1H).

LC-MS (method 1): $R_t$=1.22 min; MS (ESIpos): m/z=416 [M+H]$^+$.

3. Assays

Human ACC1 Enzyme Assay

The ACC1 inhibition data were obtained using two different assays (A1 and B 1)

Assay A1 (=(A1))

The inhibitory activity of the substances of this invention with regard to acetyl-CoA carboxylase 1 (ACC1) was measured using the ACC1 assay described in the paragraphs below. The basic principle of the assay is the measurement of adenosine diphosphate (ADP), which is formed as a by-product, by means of an HTRF®-based competitive immunoassay (HTRF=Homogeneous Time Resolved Fluorescence).

The enzyme used was C-terminally FLAG-tagged recombinant human ACC1 (GenBank Accession no. NM_198834, amino acids 39—end), expressed in baculovirus-transfected insect cells (Hi5) and purified by affinity chromatography on Anti-FLAG®M2 affinity gel (Sigma-Aldrich). Alternatively, it is possible to use commercial C-terminally His-tagged ACC1 from BPS Bioscience (San Diego, Calif., catalogue no. 50200, amino acids 39 —end). For the assay, 50 nl of a 100-fold concentrated solution of the test substance in DMSO were pipetted into a black low-volume 384-well microtitre plate (Greiner Bio-One, Frickenhausen, Germany), 2 μl of a solution of ACC1 in assay buffer [50 mM HEPES/NaOH pH 7.5, 12 mM sodium bicarbonate, 2 mM $MgCl_2$, 2 mM potassium citrate, 0.005% (w/v) bovine serum albumin (BSA)] were added and the mixture was incubated for 15 min to allow pre-binding of the substances to the enzyme prior to the enzyme reaction. The enzyme reaction was then started by addition of 3 μl of a solution of adenosine triphosphate (ATP, 83.5 μM=>the final concentration in 5 μl assay volume is 50 μM, Amersham Pharmacia Biotech #27-2056-01) and acetyl-CoA (33.4 μM=>the final concentration in 5 μl assay volume is 20 μM, Roche Bioscience #10101893001) in assay buffer, and the resulting mixture was incubated at 22° C. for a reaction time of 20 min. The concentration of the ACC1 was adjusted to the respective activity of the enzyme and set such that the assay was carried out in the linear range. Typical concentrations were in the range of 2.5 ng/μl.

The reaction was stopped by successive addition of 2.5 μl of a solution of d2-labelled ADP (HTRF® Transscreener™ ADP kit, C is biointernational, Marcoule, France) in EDTA-containing HTRF® Transscreener™ ADP detection buffer (contained in the HTRF® Transscreener™ ADP kit, 50 mM HEPES pH 7.0, 60 mM EDTA, 0.1% (w/v) BSA, 0.02% sodium azide, 400 mM potassium fluoride) and 2.5 μl of a solution of europium cryptate-labelled anti-ADP antibody (HTRF® Transscreener™ ADP kit) in HTRF® Transscreener™ ADP detection buffer.

The resulting mixture was incubated at 22° C. for 1 h to allow binding of the europium cryptate-labelled anti-ADP antibody to the ADP formed by the enzyme reaction and the d2-labelled ADP. The amount of complex of d2-labelled ADP and europium cryptate-labelled anti-ADP antibody was then determined by measuring the resonance energy transfer of europium cryptate to d2. To this end, the fluorescence emissions at 620 nm and 665 nm after excitation at 350 nm were measured in an HTRF measuring instrument, for example a Rubystar or Pherastar (both BMG Labtechnologies, Offenburg, Germany). The ratio of the emissions at 665 nm and at 622 nm was taken as a measure of the amount of the complex of d2-labelled ADP and europium cryptate-labelled anti-ADP antibody and thus indirectly as a measure for the amount of unlabelled ADP formed in the enzyme reaction (higher ratio of the emissions at 665 nm and at 622 nm ⇔ more complex of d2-labelled ADP and europium cryptate-labelled anti-ADP antibody ⇔ less ADP). The data were normalized (enzyme reaction without inhibitor=0% inhibition, all other assay components but no enzyme=100% inhibition). The test substances were usually tested on the same microtitre plates at 10 different concentrations in the range from 20 μM to 1 nM (20 μM, 6.7 μM, 2.2 μM, 0.74 μM, 0.25 μM, 82 nM, 27 nM, 9.2 nM, 3.1 nM and 1 nM, the dilution series were prepared prior to the assay based on the 100-times concentrated solution by serial 1:3 dilutions) in two replications for each concentration, and IC50 values were calculated with a 4-parameter fit using an inhouse software.

Assay B1 (=(B1))

The hACC1-inhibitory action of the substances of the present invention was measured in the hACC 1 assay described in the paragraphs below.

Essentially, the enzyme activity is measured by quantifying the adenosine diphosphate (ADP) formed as a byproduct of the enzyme reactions using the ADP-Glo™ detection system from Promega. In this test, initially the adenosine triphosphate (ATP) not consumed in the enzyme reaction is converted quantitatively with an adenylate cyclase ("ADP-GLO reagent") into cAMP, the adenylate cyclase is then stopped and ("kinase detection reagent") the ADP formed is subsequently converted into ATP, which is converted in a luciferase-based reaction into a glow luminescence signal.

The enzyme used was recombinant C-terminal FLAG-tagged human ACC1 (acetyl-coenzyme A carboxylase alpha transcript variant 1) (GenBank Accession No. NM_198834) (amino acids 39—end) expressed in baculovirus-infected insect cells (Hi5) and purified by anti-FLAG affinity chromatography.

For the assay, 50 nl of a 100-times concentrated solution of the test substance in DMSO were pipetted into a white low-volume 384-well microtitre plate (Greiner Bio-One, Frickenhausen, Germany), 2.5 µl of a solution of hACC1 in assay buffer [50 mM HEPES/NaOH pH 7.5, 2 mM MgCl$_2$, 2 mM potassium citrate, 12 mM NaHCO$_3$, 2 mM dithiothreitol (DTT), 0.005% (w/v) bovine serum albumin (BSA)] were added and the mixture was incubated for 15 min to allow prebinding of the substances to the enzyme prior to the enzyme reaction. The enzyme reaction was then started by addition of 2.5 µl of a solution of adenosine triphosphate (ATP, 100 µM=>final concentration in 5 µl of assay volume: 50 µM) and acetyl-CoA (20 µM=>final concentration in 5 µl assay volume: 10 µM) in assay buffer, and the resulting mixture was incubated at 22° C. for the reaction time of 45 min. The concentration of the hACC1 was adapted to the respective activity of the enzyme and adjusted such that the assay operated in the linear range. Typical concentrations were in the range of 1.75 ng/µl. The reaction was stopped by addition of 2.5 µl of the "ADP-GLO reagent" (1:1.5-times diluted), and the resulting mixture was incubated at 22° C. for 1 h to convert the unreacted ATP completely into cAMP. 2.5 µl of the "kinase detection reagent" were then added (1.2-times more concentrated than recommended by the manufacturer), the resulting mixture was incubated at 22° C. for 1 h and the luminescence was then measured using a suitable measuring instrument (Viewlux or Topcount from Perkin-Elmer or Pherastar from BMG Labtechnologies). The amount of light emitted was taken as a measure for the amount of ADP formed and thus for the enzyme activity of the hACC1. The data were normalized (enzyme reaction without inhibitor=0% inhibition, all other assay components but no enzyme=100% inhibition). Usually, the test substances were tested on the same microtitre plates at 10 different concentrations in the range from 20 µM to 1 nM (20 µM, 6.7 µM, 2.2 µM, 0.74 µM, 0.25 µM, 82 nM, 27 nM, 9.2 nM, 3.1 nM and 1 nM, the dilution series were prepared before the assay based on the 100-times concentrated solution by serial 1:3 dilutions) in two replications for each concentration, and the IC$_{50}$ values were calculated with a 4-parameter fit using an inhouse software.

Human ACC2 Enzyme Assay

The ACC2 inhibition data were obtained using two different assays (A2 and B2)

Assay A2 (=(A2))

The inhibitory activity of the substances of this invention with regard to acetyl-CoA carboxylase 2 (ACC2) was measured using the ACC2 assay described in the paragraphs below. The basic principle of the assay is the measurement of adenosine diphosphate (ADP), which is formed as a by-product, by means of an HTRF®-based competitive immunoassay (HTRF=Homogeneous Time Resolved Fluorescence).

The enzyme used was commercially available C-terminally His-tagged ACC2 from BPS Bioscience (San Diego, Calif., catalogue no. 50201, amino acids 39—end, expressed in baculovirus-transfected Sf9 insect cells and purified by Ni-NTA affinity chromatography).

For the assay, 50 nl of a 100-fold concentrated solution of the test substance in DMSO were pipetted into a black low-volume 384-well microtitre plate (Greiner Bio-One, Frickenhausen, Germany), 2 µl of a solution of ACC2 in assay buffer [50 mM HEPES/NaOH pH 7.5, 12 mM sodium bicarbonate, 2 mM MgCl$_2$, 2 mM potassium citrate, 0.005% (w/v) bovine serum albumin (BSA)] were added and the mixture was incubated for 15 min to allow pre-binding of the substances to the enzyme prior to the enzyme reaction. The enzyme reaction was then started by addition of 3 µl of a solution of adenosine triphosphate (ATP, 83.5 µM=>the final concentration in 5 µl assay volume is 50 µM, Amersham Pharmacia Biotech #27-2056-01) and acetyl-CoA (33.4 µM=>the final concentration in 5 µl assay volume is 20 µM, Roche Bioscience #10101893001) in assay buffer, and the resulting mixture was incubated at 22° C. for a reaction time of 20 min. The concentration of the ACC2 was adjusted to the respective activity of the enzyme and set such that the assay was carried out in the linear range. Typical concentrations were in the range of 0.6 ng/µl.

The reaction was stopped by successive addition of 2.5 µl of a solution of d2-labelled ADP (HTRF® Transscreener™ ADP kit, C s biointernational, Marcoule, France) in EDTA-containing HTRF® Transscreener™ ADP detection buffer (contained in the HTRF® Transscreener™ ADP kit, 50 mM HEPES pH 7.0, 60 mM EDTA, 0.1% (w/v) BSA, 0.02% sodium azide, 400 mM potassium fluoride) and 2.5 µl of a solution of europium cryptate-labelled anti-ADP antibody (HTRF® Transscreener™ ADP kit) in HTRF® Transscreener™ ADP detection buffer.

The resulting mixture was incubated at 22° C. for 1 h to allow binding of the europium cryptate-labelled anti-ADP antibody to the ADP formed by the enzyme reaction and the d2-labelled ADP. The amount of complex of d2-labelled ADP and europium cryptate-labelled anti-ADP antibody was then determined by measuring the resonance energy transfer of europium cryptate to d2. To this end, the fluorescence emissions at 620 nm and 665 nm after excitation at 350 nm were measured in an HTRF measuring instrument, for example a Rubystar or Pherastar (both BMG Labtechnologies, Offenburg, Germany). The ratio of the emissions at 665 nm and at 622 nm was taken as a measure of the amount of the complex of d2-labelled ADP and europium cryptate-labelled anti-ADP antibody and thus indirectly as a measure for the amount of unlabelled ADP formed in the enzyme reaction (higher ratio of the emissions at 665 nm and at 622 nm ⇔ more complex of d2-labelled ADP and europium cryptate-labelled anti-ADP antibody ⇔ less ADP). The data were normalized (enzyme reaction without inhibitor=0% inhibition, all other assay components but no enzyme=100% inhibition). The test substances were usually tested on the same microtitre plates at 10 different concentrations in the range from 20 µM to 1 nM (20 µM, 6.7 µM, 2.2 µM, 0.74 µM, 0.25 µM, 82 nM, 27 nM, 9.2 nM, 3.1 nM and 1 nM, the dilution series were prepared prior to the assay based on the 100-times concentrated solution by serial 1:3 dilutions) in two replications for each concentration, and IC50 values were calculated with a 4-parameter fit using an inhouse software.

Assay B2 (=(B2))

The hACC2-inhibitory action of the substances of the present invention was measured in the hACC2 assay described in the paragraphs below.

Essentially, the enzyme activity is measured by quantifying the adenosine diphosphate (ADP) formed as a byproduct of the enzyme reactions using the ADP-Glo™ detection system from Promega. In this test, initially the adenosine triphosphate (ATP) not consumed in the enzyme reaction is converted quantitatively with an adenylate cyclase ("ADP-GLO reagent") into cAMP, the adenylate cyclase is then stopped and ("kinase detection reagent") the ADP formed is subsequently converted into ATP, which is converted in a luciferase-based reaction into a glow luminescence signal.

The enzyme used was recombinant C-terminal FLAG-tagged human ACC2 (acetyl-coenzyme A carboxylase 2) (GenBank Accession No. NP_001084) (amino acids 27—end) expressed in baculovirus-infected insect cells (Hi5) and purified by anti-FLAG affinity chromatography.

For the assay, 50 nl of a 100-times concentrated solution of the test substance in DMSO were pipetted into a white low-volume 384-well microtitre plate (Greiner Bio-One, Frickenhausen, Germany), 2.5 μl of a solution of hACC2 in assay buffer [50 mM HEPES/NaOH pH 7.5, 2 mM $MgCl_2$, 2 mM potassium citrate, 12 mM $NaHCO_3$, 2 mM dithiothreitol (DTT), 0.005% (w/v) bovine serum albumin (BSA)] were added and the mixture was incubated for 15 min to allow prebinding of the substances to the enzyme prior to the enzyme reaction. The enzyme reaction was then started by addition of 2.5 μl of a solution of adenosine triphosphate (ATP, 100 μM=>final concentration in 5 μl of assay volume: 50 μM) and acetyl-CoA (20 μM=>final concentration in 5 μl assay volume: 10 μM) in assay buffer, and the resulting mixture was incubated at 22° C. for the reaction time of 45 min. The concentration of the hACC2 was adapted to the respective activity of the enzyme and adjusted such that the assay operated in the linear range. Typical concentrations were in the range of 2 ng/μl. The reaction was stopped by addition of 2.5 μl of the "ADP-GLO reagent" (1:1.5-times diluted), and the resulting mixture was incubated at 22° C. for 1 h to convert the unreacted ATP completely into cAMP. 2.5 μl of the "kinase detection reagent" were then added (1.2-times more concentrated than recommended by the manufacturer), the resulting mixture was incubated at 22° C. for 1 h and the luminescence was then measured using a suitable measuring instrument (Viewlux or Topcount from Perkin-Elmer or Pherastar from BMG Labtechnologies). The amount of light emitted was taken as a measure for the amount of ADP formed and thus for the enzyme activity of the hACC2. The data were normalized (enzyme reaction without inhibitor=0% inhibition, all other assay components but no enzyme=100% inhibition). Usually, the test substances were tested on the same microtitre plates at 10 different concentrations in the range from 20 μM to 1 nM (20 μM, 6.7 μM, 2.2 μM, 0.74 μM, 0.25 μM, 82 nM, 27 nM, 9.2 nM, 3.1 nM and 1 nM, the dilution series were prepared before the assay based on the 100-times concentrated solution by serial 1:3 dilutions) in two replications for each concentration, and the $IC_{50}$ values were calculated with a 4-parameter fit using an inhouse software.

Non-human ACCase Assay

The assay was carried out at room temperature in a transparent 384-well microtitre plate. It determined the inorganic phosphate released from the ATP in the ACCase reaction. The test mixture contained 50 mM Tris-HCl pH 8.3, 50 mM KCl, 2.5 mM $MgCl_2$, 0.5 mM ATP, 0.8 mM dithiothreitol (DTT), 30 mM $NaHCO_3$, 0.1 mM acetyl-CoA, 0.04% bovine serum albumin and 0.4 μg partially purified ACCase enzyme in a final volume of 40 μl. After 45 minutes of incubation, the reaction was stopped with 150 μl of malachite green solution, and the absorption at 620 was read after 30 minutes.

The malachite green (MG) solution was prepared by mixing 3 parts of 0.6 mM MG-HCl solution in distilled water with 1 part of 8.5 mM ammonium molybdate in 4 M HCl. The solution was allowed to stand for 30 minutes. After filtration through a 0.45 μm polytetrafluoroethylene (PTFE) filter, 0.1 part of Triton X-100 (1.5%) in distilled water was added.

ACCase enzyme was extracted from oat seedlings 9 days after sowing and partially purified by precipitation with 0-40% ammonium sulphate followed by ion exchange chromatography on Q-Sepharose.

Mode-of-action Experiment

Prior to the determination of the activity in the MCF-7 model, some of the test substances were examined in a "mode of action" experiment. The principle of this experiment is that short-term application of a test substance capable of inhibiting ACC1 and/or ACC2 in a living organism after oral administration reduces malonyl-CoA in a tumour. To this end, in the experiment 2 million human MCF-7 breast cancer cells were injected subcutaneously into female nude mice (NMRI-nude (nu/nu) mice, Taconic M&B A/S, 1 day beforehand administration of a pellet for the release of oestrogen over a period of at least 60 days). Once the tumour extended to an area of about 60-70 $mm^2$, the test substance was administed orally over a period of 1-3 days, and at defined points in time the intratumour content of malonyl-CoA was then determined and compared to the vehicle control. The method is described in *Anal Chem.* 2008 Aug. 1; 80(15):5736-42. Epub 2008 Jul. 9.).

Cell Assays

In accordance with the invention, the substances were tested in cell-based assays for the ability of the substances of inhibiting tumour cell proliferation after a 96-hour incubation with the substance. Cell viability was tested using the Cell-Titer-Glo® luminescent cell viability assay (Promega). The cells were sown at a density of 2000-5000 cells/well (depending on the cell line) in 100 μl growth medium on 96-well microtitre plates. For each cell line examined, cells were sown on a separate plate to determine the luminescence at t=0 hours and t=96 hours. After overnight incubation at 37° C., the luminescence values for the t=0 samples were determined. The dose plates for the t=96 hours points in time were treated with substances diluted with growth medium. The cells were then incubated at 37° C. for 96 hours, and the luminescence values for the t=96 hours sample were then determined/For data analysis, the t=0 values were subtracted from the t=96 hour values for treated and untreated samples. The differences in luminescence in percent between substance-treated samples and control values were used to determine the growth inhibition in percent.

The substances were tested in the following cell lines which represent the stated indications in an exemplary manner:

| Cell line | Source | Indication |
|---|---|---|
| MCF7 | ATCC | hormone receptor-positive breast carcinoma |
| PC3 | ATCC | prostate carcinoma |
| Du145 | NCI | prostate carcinoma |
| ECC1 | ATCC | endometrial carcinoma |
| KM12 | NCI | colorectal carcinoma |
| HEC1A | ATCC | endometrial carcinoma |
| DNA-G | CLS | pancreas carcinoma |
| BxPC3 | ATCC | pancreas carcinoma |
| H460 | ATCC | non-small cell bronchial carcinoma |
| CAL-120 | ATCC | hormone receptor-negative breast carcinoma |
| BT-20 | ATCC | hormone receptor-negative breast carcinoma |
| SNU16 | ATCC | stomach carcinoma |
| LNCaP | ATCC | prostate carcinoma |

Xenograft Model

Xenograft models in immunosuppressed mice were used to determine the antitumour activity in living organisms.

To this end, initially the maximum tolerable dose (MTD) was determined using the following protocol:

Over a period of 1, 2 or 3 weeks, a defined dose of the test substance was administered orally to female nude mice (NMRI-nude (nu/nu) mice, Taconic M&B A/S), and the mice were observed daily for mortality and body weight. The MTD was defined as the highest dose which could be administered without any animal dying during the treatment phase and the 7-day additional observation phase, and without any body weight loss of more than 10% compared to the initial weight.

Various xenograft models in which the test substances were administered in their MTD and in lower doses were then used to determine the antitumour activity. In addition to various other models, use was made primarily of the breast cancer model with hormone-dependent human MCF-7 cells in female nude mice (NMRI-nude (nu/nu) mice, Taconic M&B A/S). To this end, on the day prior to the implantation of the tumour cells, a pellet for releasing oestrogen (17β-oestradiol 0.36 mg, release over 60 days) was administered subcutaneously to the mice. The next day, 2 million tumour cells (suspended in medium+Matrigel) 1:1, final 0.1 ml) were then injected subcutaneously into the side of each animal. When the tumours extended to an area of 20-25 mm$^2$, the mice were randomized into therapy groups and therapy was initiated. The therapy was then continued until an average tumour size of 120 mm$^2$ had been reached in the control group, which had only been given the vehicle of the test substance, or in one of the treatment groups, with tumour area and body weight being measured 2-3 times per week. At this point in time, the experiment was terminated in all groups and the excised tumours were weighed.

The T/C value was calculated as primary success parameter either using the effect on the tumour weight or using the effect on the tumour area: mean tumour weight/area in the treatment group divided by mean of the tumour weight/area in the vehicle group.

Analysis of the ACC1 Expression in Tumour Tissue and Normal Tissue

The ACC1 expression was determined using a microarray. To this end, the RNA of various tumour tissues and the corresponding normal tissues was isolated. The method made use of Trizol RNA extraction reagent (Invitrogen) and subsequent purification using the RNeasy mini kit (Qiagen). Moreover, a DNase I (Qiagen) digestion was carried out to eliminate genomic DNA. For quality control, the total RNA was analyzed with the aid of an RNA LabChip on an Agilent Bioanalyzer 2100 Platform (Agilent Technologies), and the RNA concentration was determined using the Peqlab Nano-Drop system. For hybridization, the one-cycle eukaryotic target labelling assay from Affymetrix was used, and the array was then read on an AffymetrixGeneChip 3000 scanner (Affymetrix). Evaluation and quality control were carried out using the Expressionist Pro 4.0 Refiner (GeneData) software.

4. Results

4.1. Enzyme Assay

Table 1 summarizes the results for compound A and the comparative examples from the enzyme assays.

TABLE 1

| Example No. | ACC 1 (=A1) IC50 [μmol/l] | ACC 2 (=A2) IC50 [μmol/l] | ACC 1 (=B1) IC50 [μmol/l] | ACC 2 (=B2) IC50 [μmol/l] |
|---|---|---|---|---|
| C.1 | 0.28 | 0.37 | 0.084 | 0.822 |
| C.2 | 0.327 | 1.414 | 0.428 | 2.61 |
| A | 0.129 | 0.690 | 0.102 | 1.38 |

These values show that compound A and Comparative Example C 1 inhibit the enzymes in a comparatively strong manner, whereas Comparative Example C.2 is inferior.

4.2 Cell Assays

Table 2 summarizes the results of the cell assays with respect to compound A and the Comparative Examples.

TABLE 2

| Example No. | MCF7 IC50 [μmol/l] | PC 3 IC50 [μmol/l] | Du145 IC50 [μmol/l] | ECC1 IC50 [μmol/l] | KM12 IC50 [μmol/l] | HEC-1A IC50 [μmol/l] |
|---|---|---|---|---|---|---|
| C.1 | 0.057 | | | | | |
| C.2 | 0.270 | | | | | |
| A | 0.037 | 0.025 | 0.039 | 0.221 | 0.275 | 1.76 |

| Example No. | CAL-120 IC50 [μmol/l] | BT-20 IC50 [μmol/l] | LNCaP IC50 [μmol/l] | BxPC3 IC50 [μmol/l] | DAN-G IC50 [μmol/l] | SNU16 IC50 [μmol/l] | H460 IC50 [μmol/l] |
|---|---|---|---|---|---|---|---|
| C.1 | | | | | | | |
| C.2 | | | | | | | |
| A | 0.266 | 0.187 | 0.334 | 0.165 | 0.184 | 0.164 | 0.201 |

4.3 Maximum Tolerated Dose (MTD)

Comparative Example C.1

Comparative Example C.1 was administered to female nude mice (NMRI nu/nu):
Dose: see Tab. 3
Mode of administration: oral
Vehicle: PEG400/ethanol/Solutol HS 15(70/5/25, v/v/v)
  (Solutol HS15: polyoxyethylene ester of 12-hydroxystearic acid)
Administration volume: 10 ml/kg
Scheme: see Tab. 3

The treatment phase was followed by an observation phase of 7 days. The deaths that occurred during this period and the effect on the bodyweight are summarized in Table 3.

TABLE 3

| Substance | Dose (mg/kg) | Scheme | Bodyweight (%) | Deaths |
|---|---|---|---|---|
| C.1 | 10 | 14 days, 2 times a day | minus 12 | 1 of 3 |
| C.1 | 20 | 14 days, 2 times a day | minus 29 | 2 of 3 |
| C.1 | 30 | 14 days, 2 times a day | minus 11 | 2 of 3 |
| Vehicle | | 21 days, once per day | plus 15 | 0 of 5 |
| C.1 | 15 | 21 days, once per day | minus 1 | 1 of 5 |
| C.1 | 20 | 21 days, once per day | minus 2 | 1 of 5 |
| C.1 | 25 | 21 days, once per day | minus 3 | 1 of 5 |

Accordingly, the MTD for a 14-day treatment with 2 administrations per day was less than 10 mg/kg.

Accordingly, the MTD for a 21-day treatment with 1 administration per day was less than 15 mg/kg.

Since deaths and bodyweight loss did occur in all groups, it was not possible to determine the MTD.

Comparative Example C.1 was subsequently administered to female nude mice (NMRI nu/nu) in the MCF-7 breast cancer xenograft model:
Dose: 7.5 mg/kg
Mode of administration: oral
Vehicle: PEG400/ethanol/Solutol HS 15(70/5/25, v/v/v)
Administration volume: 10 ml/kg
Scheme: 27 days, 2 times per day (2 qd)
Mice: 10

Up to day 37 of the experiment, this dose was tolerated relatively well (low bodyweight loss, 1 of 10 animals died). In this dose group, a therapeutic efficacy, defined as a T/C value of $\leq$0.5, could not be observed compared to the vehicle control (T/C value based on tumour area=0.86).

Figure 2:
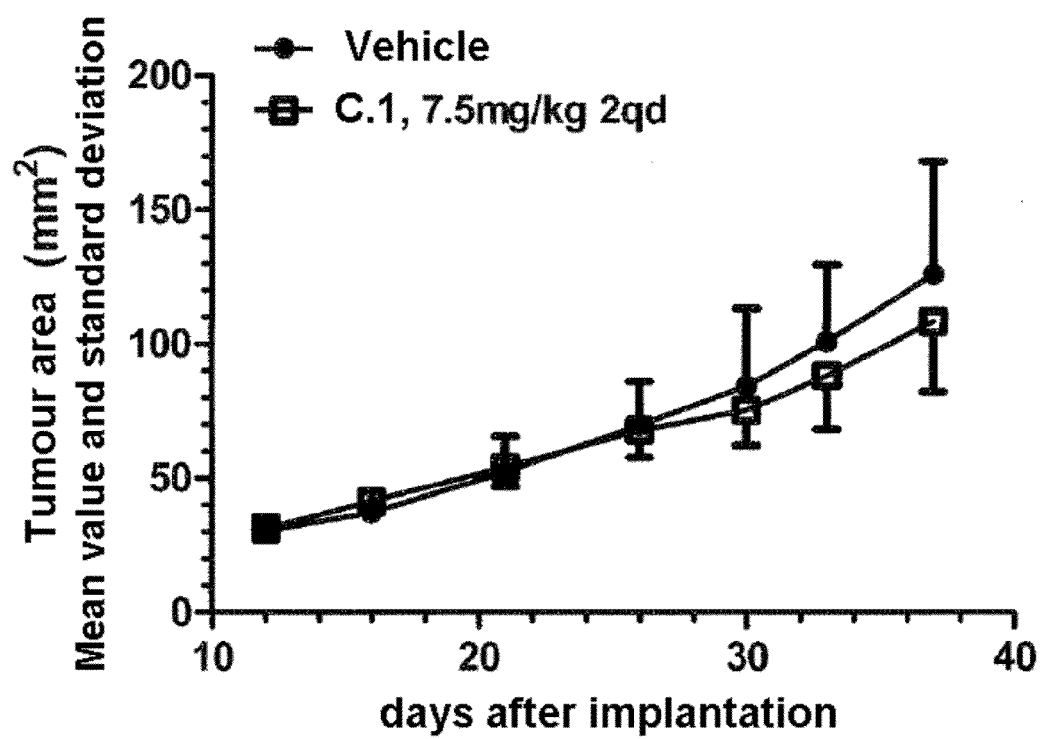

FIG. 2 shows the tumour area as a function of the number of days after implantation of the tumour cells.

The treatment of the remaining animals was continued with 10 mg/kg 2 qd or 12.5 mg/kg 2 qd up to day 43. However, these two higher dosage schemes were tolerated poorly (1 of 4 or 4 of 5 deaths respectively).

To summarize: the therapeutic window of Comparative Example C.1, if present, has to be assumed to be very small.

Compound A

Compound A was administered to female nude mice (NMRI nu/nu):
Dose: see Tab. 4
Mode of administration: oral
Vehicle: PEG400/ethanol/Solutol HS 15(70/5/25, v/v/v)
Administration volume: 10 ml/kg
Scheme: see Tab. 4

The treatment phase was followed by an observation phase of 7 days. The deaths that occurred during this period and the effect on the bodyweight are summarized in Table 4.

TABLE 4

| Substance | Dose (mg/kg) | Scheme | Bodyweight (%) | Deaths |
|---|---|---|---|---|
| Vehicle | | 21 days, once per day | plus 5 | 0 of 5 |
| Compound A | 20 | 21 days, once per day | plus 2 | 0 of 5 |
| Compound A | 30 | 21 days, once per day | plus 1 | 0 of 5 |
| Compound A | 40 | 21 days, once per day | minus 3 | 1 of 5 |
| Compound A | 50 | 21 days, once per day | minus 29 | 5 of 5 |
| Compound A | 60 | 21 days, once per day | minus 24 | 5 of 5 |

Accordingly, the MTD for a 21-day treatment with 1 administration per day was less than 40 mg/kg and above 30 mg/kg.

Compound A was subsequently administered to female nude mice (NMRI nu/nu) in the MCF-7 breast cancer xenograft model:
Dose: see Tab. 5
Mode of administration: oral
Vehicle: PEG400/ethanol/Solutol HS 15(70/5/25, v/v/v)
Administration volume: 10 ml/kg
Scheme: 30 days, once per day (qd)
Mice per dose group: 10-13

TABLE 5

| Substance | Dose (mg/kg) | T/C (based on tumour area) | T/C (based on tumour weight) |
|---|---|---|---|
| Vehicle | | 1.00 | 1.00 |
| Compound A | 20 | 0.56 (ns) | 0.42 (p = 0.003) |
| Compound A | 25 | 0.51 (p < 0.05) | 0.37 (p < 0.001) |
| Compound A | 30 | 0.49 (p < 0.05) | 0.35 (p < 0.001) |
| Compound A | 35 | 0.44 (p < 0.05) | 0.31 (p < 0.001) |

For the statistical evaluation of the experiment, the non-parametric ANOVA test was used for the T/C values based on the tumour area, since there was no normal distribution of the measured values. All therapy groups were then compared to the vehicle group using Dunns Post test. The resulting p values are shown in the table (ns: not significant=p>0.05). Since there was a normal distribution of the T/C values based on tumour weight, the ANOVA test for parametric values was used for analysis. All therapy groups were then compared to the vehicle group using the Bonferroni Post test. The resulting p values are shown in Table 5.

Since all dose groups used reached the target value of a T/C (based on tumour weight) of <0.5 in this experiment, the experiment was evaluated statistically, the results of the evaluation also being shown in Table 5. Compound A inhibited in a statistically significant manner tumour growth (based both on tumour weight and tumour area) above a dose of 25 mg/kg when administered once per day. Based on tumour weight, this effect was statistically significant even from a dose of 20 mg/kg, administered once per day.

Figure 3:
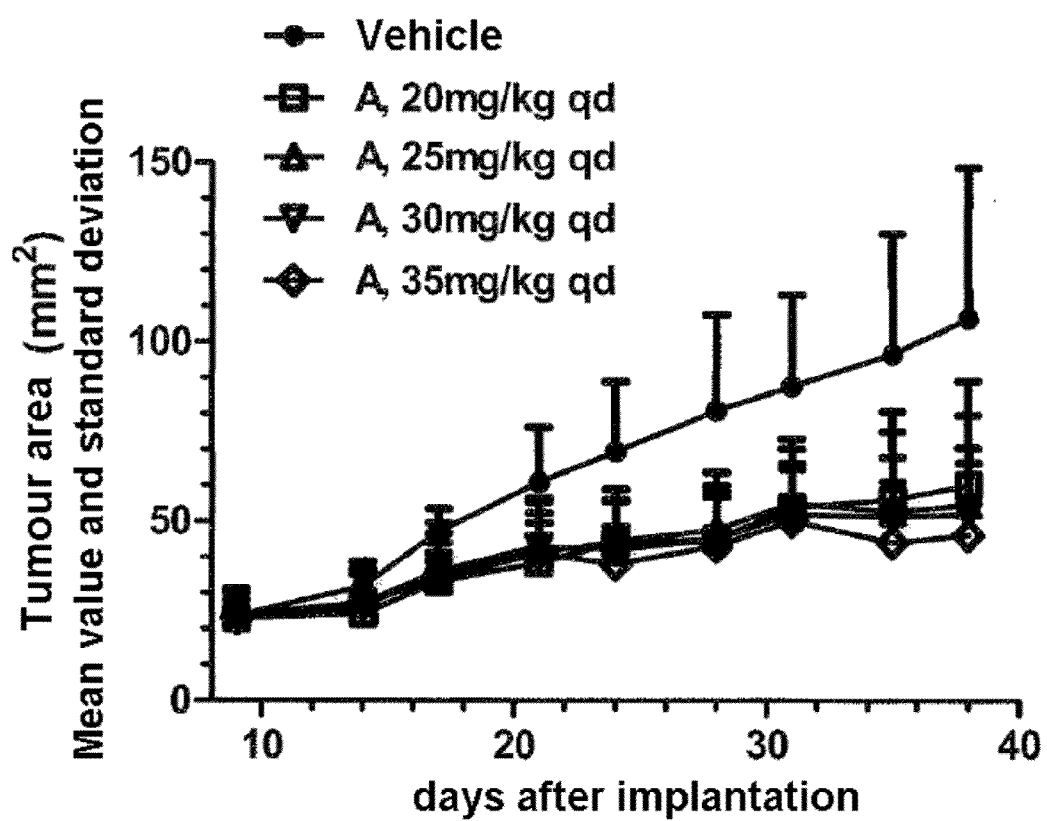

FIG. 3 shows the tumour area as a function of the number of days after implantation of the tumour cells.

Accordingly, comparison of Comparative Example C.1 and compound A shows that Comparative Example C.1 showed no antitumoral efficacy even at a dose which is not tolerated well, whereas biologically meaningful and significant antitumoral effects were found for compound A in a tolerated dose range of 20 mg/kg qd to 35 mg/kg qd.

ACC1 Expression in Tumour and Normal Tissue

The ACC 1 expression in tumour and corresponding normal tissue was determined by microarray (FIG. 1). In mamma carcinoma, colorectal carcinoma, bronchial carcinoma and pancreas carcinoma, the expression of ACC1 was upregulated significantly compared to normal tissue.

5. Formulation

Tablets comprising Compound A a) Preparation of the Pharmaceutical Formulation by Direct Tabletting Tablets according to the composition from Table 6 comprising Compound A were prepared by direct tabletting.

TABLE 6

| Starting materials | Mass/Tablet [mg] |
|---|---|
| Compound A | 80.0 |
| mannitol, spray-dried | 67.0 |
| cellulose, microcrystalline | 40.0 |
| Na-croscarmellose | 10.0 |
| magnesium stearate | 3.0 |
| total | 200.0 |

The pharmaceutical formulation can be prepared by suitable processes, in particular by powder mixing and direct tabletting, in any scale.

To prepare 50 tablets,

| | |
|---|---|
| 3.351 g | of mannitol, spray-dried |
| 2.004 g | of cellulose, microcrystalline |
| 0.499 g | of Na-croscarmellose and |
| 3.992 g | of exemplary compound 1-118 | were premixed in a mortar by careful grinding. The mixture was transferred into a 100-ml screw-cap tube and homogenized in a Turbula mixer for 10 minutes. After addition of 0.149 g of magnesium stearate, the mixture was mixed in the Turbula mixer for another 1 min.

The moulding material obtained in this manner was tabletted in an eccentric tablet press (Korsch EK 2) to give biconvex tablets of a diameter of 8 mm and a curvature of 12 mm.

b) Break Force

Break force (using a Schleuniger break force tester), mass and disintegration time in water at 37° C. (using the apparatus described in the monograph 2.9.1 European Pharmacopoeia) of the tablets obtained was tested at the beginning, in the middle and at the end of the tabletting process.

| | Break force | Mass | Disintegration time |
|---|---|---|---|
| beginning | 81N | 198.7 mg | 1:28 min |
| middle | 95N | 196.8 mg | 1:28 min. |
| end | 97N | 199.0 mg | 1:32 min. |
| mean | 91N | 198.2 mg | 1:29 min. | c) In-vitro Dissolution

The in vitro release of Compound A from the tablets prepared was determined using apparatus 2 (paddle method) in accordance with USP. The release test was in each case carried out in 900 ml of various media at 37° C. and with a stirrer speed of 75 rotations per minute. Each determination was carried out in three replications. The content was determined by HPLC. The results are shown in Table 7 and FIG. 4.

TABLE 7

| | % released after | | | | |
|---|---|---|---|---|---|
| Medium | 15 min | 30 min | 45 min | 60 min | 90 min |
| 0.1N HCl + 1% SDS* (pH 1) | 20.5% | 32.1% | 37.1% | 41.2% | 45.3% |
| USP phosphate buffer pH = 6.8 + 1% SDS* | 43.2% | 55.6% | 62.0% | 65.7% | 70.1% |
| USP phosphate buffer pH = 8.0 | 80.1% | 87.5% | 89.6% | 90.4% | 91.2% |

*SDS = sodium laurylsulphate (added because of insufficient solubility at pH 1 and pH 6.8)

d) Short-term Stability of the Pharmaceutical Formulation

The finished tablets were subjected to a 1-month short-term stability test at 25° C./60% relative humidity and at 40° C./75% relative humidity. Under either conditions, the tablets were stable with respect to content and degradation products, examined by HPLC.

FIGURES

FIG. 1: ACC1 expression in tumour tissue and corresponding normal tissue

1: healthy breast tissue (2 samples)
2: breast tumour tissue (26 samples)
3: healthy colon tissue (30 samples)
4: colon tumour tissue (71 samples)
5: healthy lung tissue (27 samples)
6: lung tumour tissue (40 samples)
7: healthy pancreas tissue (22 samples)
8: pancreas tumour tissue (19 samples)

FIG. 2: Therapeutic efficacy of Comparative Example C.1 in the hormone-dependent MCF-7 breast cancer xenograft model.

FIG. 3: Therapeutic efficacy of Compound A in the hormone-dependent MCF-7 breast cancer xenograft model.

Figure 4:
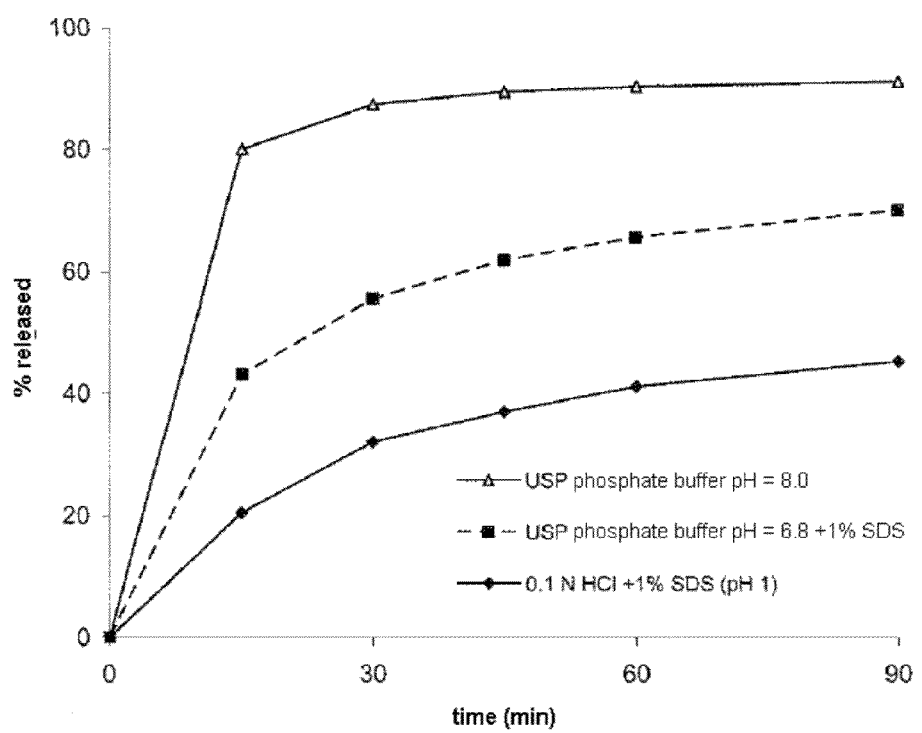

FIG. 4: Release curve of Compound A from tablets

The invention claimed is:

1. A method for the therapy of a tumour disorder comprising administering to a human or mammal in need thereof an effective amount of (5s,8s)-3-(4'-chloro-3'-fluoro-4-methyl-biphenyl-3-yl)-4-hydroxy-8-methoxy-1-azaspiro[4.5]dec-3-en-2-one.

2. The method according to claim 1, wherein the tumour disorder is selected from breast carcinomas, pancreas carcinomas, non-small cell bronchial carcinomas, endometrial carcinomas, colorectal carcinomas, stomach carcinomas, and prostate carcinomas.

* * * * *